United States Patent [19]

Cormier et al.

[11] Patent Number: 5,292,658

[45] Date of Patent: Mar. 8, 1994

[54] CLONING AND EXPRESSIONS OF RENILLA LUCIFERASE

[75] Inventors: Milton J. Cormier, Bogart; William W. Lorenz, Athens, both of Ga.

[73] Assignee: University of Georgia Research Foundation, Inc. Boyd Graduate Studies Research Center, Athens, Ga.

[21] Appl. No.: 79,700

[22] Filed: Jun. 17, 1993

Related U.S. Application Data

[63] Continuation of Ser. No. 933,017, Aug. 20, 1992, abandoned, which is a continuation of Ser. No. 458,952, Dec. 29, 1989, abandoned.

[51] Int. Cl.$^5$ .................... C12N 15/53; C12N 15/70; C12N 9/02
[52] U.S. Cl. ............................ 435/252.33; 435/69.1; 435/189; 435/320.1; 435/252.3; 536/23.2; 935/14; 935/66; 935/73
[58] Field of Search ................ 435/69.1, 189, 252.3, 435/320.1; 536/23.2

[56] References Cited

U.S. PATENT DOCUMENTS

| | | | |
|---|---|---|---|
| 4,581,335 | 4/1980 | Baldwin | 435/172.3 |
| 4,965,190 | 10/1990 | Woo et al. | 435/6 |
| 4,968,613 | 11/1990 | Masuda et al. | 435/172.3 |
| 4,985,511 | 1/1991 | Geiger et al. | 435/6 |
| 5,162,227 | 11/1992 | Cormier | 435/252.33 |

FOREIGN PATENT DOCUMENTS 8703304 6/1987 World Int. Prop. O. .... C12P 21/00

OTHER PUBLICATIONS

"Luciferases from Different Species of Fireflies are Antigenically Similar," by G. Wienhausen and M. DeLuca in *Photochemistry and Photobiology*, 42: 609-611, (1985).

"Renilla and Aequorez biocuminescence" by M. J. Cormier, in *Bioluminescence and Chemiluminescence*, pp. 225-233 (1981).

Gherna, R. et al., Eds., 1985, American Type Culture Collection Catalogue, Sixteenth Edition, p. 255.

Matthews, J. C. et al., 1977, Biochemistry 16(1): 85-91.

Jaye, M. et al., 1983, Nucleic Acids Research, 11(8):2325-2335.

Matsuda, G. et al., 1981, FEBS Letters, 126(1): 111-113.

"Ca$^{2+}$-induced Bioluminescence in *Renilla reniformis*," by Harry Charbonneau and Milton J. Cormier in *The Journal of Biological Chemistry*, 254:769-780 (Feb. 10, 1979).

"An Energy Transfer Protein in Coelenterate Bioluminescence," by William W. Ward and Milton J. Cormier in *The Journal of Biological Chemistry*, 254:781-788 (Feb. 10, 1979).

Lorenz et al. "Isolation and Expression of a cDNA Encoding *Renilla reniformis* Luciferase" Proc. Nat'l. Acad. Sci. USA, 88: 4438-4442, (1981).

Ward, W. W. et al., "Extraction of Renilla-type luciferin from the calcium-activated photoproteins aequorin, mnemiopsin, and berovin," *Proc. Nat. Acad. Sci. USA*, vol. 72, No. 7, pp. 2530-2534, (Jul. 1975).

Stephenson, D. G. et al., "Studies on the Luminescent Response of the Ca$^{2+}$-Activated Photoprotein, Obelin," *Biochimica et Biophysica Acta*, vol. 678, pp. 65-75, (1981).

Cormier, M. J., "Mechanism of energy conversion and transfer in bioluminescence," Chemical Abstract, vol. 93, No. 5, p. 545. No. 4201H, (Aug. 4, 1980).

(List continued on next page.)

*Primary Examiner*—Robert A. Wax
*Assistant Examiner*—William W. Moore
*Attorney, Agent, or Firm*—Jones & Askew

[57] ABSTRACT

Genetic material encoding luciferase from the marine coelenterate Renilla has been isolated and characterized. This genetic material allows the production of peptides for use as labels in bioluminescence assays or can itself be directly used to identify luciferase genes from related organisms.

9 Claims, 8 Drawing Sheets

OTHER PUBLICATIONS

Hart, R. C. et al., "Mechanism of the Enzyme-Catalyzed Bioluminescent Oxidation of Coelenterate-Type Luciferin," Biochemical and Biophysical Research Communications, vol. 81, No. 3, pp. 980–986, (Apr. 14, 1978).

Hart R. C. et al., "*Renilla, Reinformis* Bioluminescense: Luficerase-Catalyzed production of Nonradiating Excited States from Luciferin Analogues and Elucidation of the Excited States . . . " Biochemistry, vol. 18, No. 11, pp. 2204–2210, (1979).

Anderson, J. M. et al., "Lumisomes: A Bioluminescent Particle Isolated from the Sea Pansy *Renilla reniformis*," Chemiluminescence and Bioluminescence, Plenum Publishing Corporation, pp. 387–392, (1973).

Cormier, M. J. et al., "Evidence for Similar Biochemical Requirements for Bioluminescence among the Coelenterates," Journal of Cellular Physiology, vol. 81, No. 2, pp. 291–297, (Apr. 1973).

Hori, K. et al., "Structure of native *Renilla reniformis* luciferin," Proc. Natl. Acad. Sci. USA, vol. 74, No. 10,, pp. 4285–4287, (Oct. 1977).

R. RENIFORMIS LUCIFERASE cDNA SEQUENCE

```
            10         20         30         40         50         60
        AGCTTAAAGA TGACTTCGAA AGTTTATGAT CCAGAACAAA GGAAACGGAT GATAACTGGT
            70         80         90        100        110        120
        CCGCAGTGGT GGGCCAGATG TAAACAAATG AATGTTCTTG ATTCATTTAT TAATTATTAT
           130        140        150        160        170        180
        GATTCAGAAA AACATGCAGA AAATGCTGTT ATTTTTTTAC ATGGTAACGC GGCCTCTTCT
           190        200        210        220        230        240
        TATTTATGGC GACATGTTGT GCCACATATT GAGCCAGTAG CGCGGTGTAT TATACCAGAT
           250        260        270        280        290        300
        CTTATTGGTA TGGGCAAATC AGGCAAATCT GGTAATGGTT CTTATAGGTT ACTTGATCAT
           310        320        330        340        350        360
        TACAAATATC TTACTGCATG GTTGAACTT CTTAATTTAC CAAAGAAGAT CATTTTTGTC
           370        380        390        400        410        420
        GGCCATGATT GGGGTGCTTG TTTGGCATTT CATTATAGCT ATGAGCATCA AGATAAGATC
           430        440        450        460        470        480
        AAAGCAATAG TTCACGCTGA AAGTGTAGTA GATGTGATTG AATCATGGGA TGAATGGCCT
           490        500        510        520        530        540
        GATATTGAAG AAGATATTGC GTTGATCAAA TCTGAAGAAG GAGAAAAAAT GGTTTTG_GAG_
           550        560        570        580        590        600
        _AATAACTTCT_ _TCGT_GGAAAC CATGTTGCCA TCAAAAATCA TGAGAAAGTT AGAACCAGAA
           610        620        630        640        650        660
        GAATTTGCAG CATATCTTGA ACCATTCAAA GAGAAGGTG AAGTTCGTCG TCCAACATTA
           670        680        690        700        710        720
        TCATGGCCTC GTGAAATCCC GTTAGTAAAA GGTGGTAAAC CTGACGTTGT ACAAATTGTT
           730        740        750        760        770        780
        AGGAATTATA ATGCTTATCT ACGTGCAAGT GATGATTTAC CAAAAATGTT TATTGAATCG
           790        800        810        820        830        840
        GATCCAGGAT TCTTTTCCAA TGCTATTGTT GAAGGCGCCA _AGAAGTTTCC_ _TAATACT_GAA
           850        860        870        880        890        900
        TTTGTCAAAG TAAAAGGTCT TCATTTTTCG CAAGAAGATG CACCTGATGA AATGGGAAAA
           910        920        930        940        950        960
        TATATCAAAT CGTTCGTTGA GCGAGTTCTC AAAAATGAAC AATAATTACT TTGGTTTTTT
           970        980        990       1000       1010       1020
        ATTTACATTT TTCCCGGGTT TAATAATATA AATGTCATTT TCAACAATTT TATTTTAACT
          1030       1040       1050       1060       1070       1080
        GAATATTTCA CAGGGAACAT TCATATATGT TGATTAATTT AGCTCGAACT TTACTCTGTC
          1090       1100       1110       1120       1130       1140
        ATATCATTTT GGAATATTAC CTCTTTCAAT GAAACTTTAT AAACAGTGGT TCAATTAATT
          1150       1160       1170       1180       1190
        AATATATATT ATAATTACAT TTGTTATGTA ATAAACTCGG TTTTATTATA AAAAAA
```

FIGURE 1

TRANSLATED RENILLA LUCIFERASE CDNA

```
                  10                                        20
SER LEU LYS MET THR SER LYS VAL TYR ASP PRO GLU GLN ARG LYS ARG MET ILE THR GLY 30                                        40
PRO GLN TRP TRP ALA ARG CYS LYS GLN MET ASN VAL LEU ASP SER PHE ILE ASN TYR TYR 50                                        60
ASP SER GLU LYS HIS ALA GLU ASN ALA VAL ILE PHE LEU HIS GLY ASN ALA ALA SER SER 70                                        80
TYR LEU TRP ARG HIS VAL VAL PRO HIS ILE GLU PRO VAL ALA ARG CYS ILE ILE PRO ASP 90                                       100
LEU ILE GLY MET GLY LYS SER GLY LYS SER GLY ASN GLY SER TYR ARG LEU LEU ASP HIS 110                                       120
TYR LYS TYR LEU THR ALA TRP PHE GLU LEU LEU ASN LEU PRO LYS LYS ILE ILE PHE VAL 130                                       140
GLY HIS ASP TRP GLY ALA CYS LEU ALA PHE HIS TYR SER TYR GLU HIS GLN ASP LYS ILE 150                                       160
LYS ALA ILE VAL HIS ALA GLU SER VAL VAL ASP VAL ILE GLU SER TRP ASP GLU TRP PRO 170                                       180
ASP ILE GLU GLU ASP ILE ALA LEU ILE LYS SER GLU GLU GLY GLU LYS MET VAL LEU GLU 190                                       200
ASN ASN PHE PHE VAL GLU THR MET LEU PRO SER LYS ILE MET ARG LYS LEU GLU PRO GLU 210                                       220
GLU PHE ALA ALA TYR LEU GLU PRO PHE LYS GLU LYS GLY GLU VAL ARG ARG PRO THR LEU 230                                       240
SER TRP PRO ARG GLU ILE PRO LEU VAL LYS GLY GLY LYS PRO ASP VAL VAL GLN ILE VAL 250                                       260
ARG ASN TYR ASN ALA TYR LEU ARG ALA SER ASP ASP LEU PRO LYS MET PHE ILE GLU SER 270                                       280
ASP PRO GLY PHE PHE SER ASN ALA ILE VAL GLU GLY ALA LYS LYS PHE PRO ASN THR GLU 290                                       300
PHE VAL LYS VAL LYS GLY LEU HIS PHE SER GLN GLU ASP ALA PRO ASP GLU MET GLY LYS

310
TYR ILE LYS SER PHE VAL GLU ARG VAL LEU LYS ASN GLU GLN
```

FIGURE 2

Recombinant Luciferase Amino Acid Sequence And Native Luciferase V-8 Protease Digested Peptides

```
1                                                                            20
  MET THR SER LYS VAL TYR ASP PRO GLU GLN ARG LYS ARG MET ILE THR GLY PRO GLN TRP 21                                                                           40
  TRP ALA ARG CYS LYS GLN MET ASN VAL LEU ASP SER PHE ILE ASN TYR TYR ASP SER GLU 41                                                                           60
  LYS HIS ALA GLU ASN ALA VAL ILE PHE LEU HIS GLY ASN ALA ALA SER SER TYR LEU TRP 61                                                                           80
  ARG HIS VAL VAL PRO HIS ILE GLU PRO VAL ALA ARG CYS ILE ILE PRO ASP LEU ILE GLY 81                                                                          100
  MET GLY LYS SER GLY LYS SER GLY ASN GLY SER TYR ARG LEU LEU ASP HIS TYR LYS TYR 101                                                                         120
  LEU THR ALA TRP PHE GLU LEU LEU ASN LEU PRO LYS LYS ILE ILE PHE VAL GLY HIS ASP 121                                                                         140
  TRP GLY ALA CYS LEU ALA PHE HIS TYR SER TYR GLU HIS GLN ASP LYS ILE LYS ALA ILE 141                                                                         160
  VAL HIS ALA GLU SER VAL VAL ASP VAL ILE GLU SER TRP ASP GLU TRP PRO ASP ILE GLU 161                                                                         180
  GLU ASP ILE ALA LEU ILE LYS SER GLU GLU GLY GLU LYS MET VAL LEU GLU ASN ASN PHE 181                                                                         200
  PHE VAL GLU THR MET LEU PRO SER LYS ILE MET ARG LYS LEU GLU PRO GLU GLU PHE ALA

201                                                                    ★ 220
  ALA TYR LEU GLU PRO PHE LYS GLU LYS GLY GLU VAL ARG ARG PRO THR LEU SER TRP PRO 221                                                                         240
  ARG GLU ILE PRO LEU VAL LYS GLY GLY LYS PRO ASP VAL VAL GLN ILE VAL ARG ASN TYR 241                                                                         260
  ASN ALA TYR LEU ARG ALA SER ASP ASP LEU PRO LYS MET PHE ILE GLU SER ASP PRO GLY 261                                                                         280
  PHE PHE SER ASN ALA ILE VAL GLU GLY ALA LYS LYS PHE PRO ASN THR GLU PHE VAL LYS 281                                                                         300
  VAL LYS GLY LEU HIS PHE SER GLN GLU ASP ALA PRO ASP GLU MET GLY LYS TYR ILE LYS

301
  SER PHE VAL GLU ARG VAL LEU LYS ASN GLU GLN
```

Peptide 1: Peptide 4:
Peptide 2: Peptide 5:
Peptide 3: Peptide 6:
Peptide 7:

FIGURE 3

*Renilla reniformis* Peptides: V-8 Protease Digested

1) GLU-GLY-ALA-|LYS-LYS-PHE-PRO-ASN-THR-|GLU

2) GLU-ARG-VAL-LEU-LYS-ASN-GLU

3) GLU-GLY-GLU-LYS-MET-VAL-LEU-GLU

4) GLU-ASP-ILE-ALA-LEU-ILE-LYS-SER-GLU

5) GLU-SER-ASP-PRO-GLY-PHE-PHE-SER-ASN-ILE-VAL-GLU

6) GLU-LYS-GLY-GLU-VAL-ARG-ARG-PRO-THR-LEU-SER-LEU-PRO-ARG-
GLU-ILE-PRO-LEU-VAL-LYS-GLY

7) |GLU-ASN-ASN-PHE-PHE-VAL-|GLU

|GLU-ASN-ASN-PHE-PHE-VAL|

Luciferase Probe #1: GAA-AAT-AAT-TTT-TTT-GT
(32 degeneracies)    G    C    C    C    C

|LYS-LYS-PHE-PRO-ASN-THR|

Luciferase Probe #2: AAA-AAA-TTT-CCT-AAT-AC
(64 degeneracies)    G    G    C    C    C
                                    A
                                    G

FIGURE 4

RESTRICTION ENZYME MAP OF RENILLA LUCIFERASE cDNA
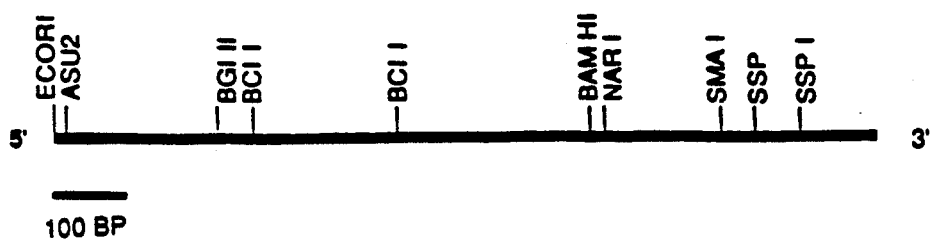
M13 SEQUENCING STRATEGY
FOR RENILLAA LUCIFERASE cDNA
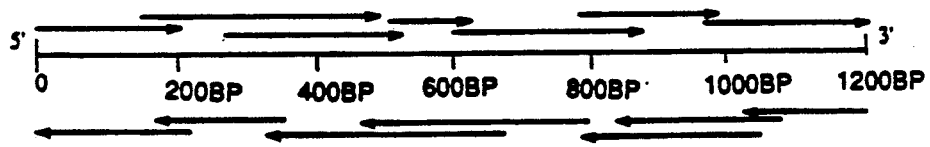
FIGURE 5

RENILLA LUCIFERASE EXPRESSION PLAMID

Purification Scheme for Recombinant Luciferase pTZRLuc-1 cells in 10mM EDTA pH8

↓ Freeze thaw once, lysozyme, DNase I, sonication

Centrifugation 48 x g, 30 min

↓ discard pellet

DEAE Sephadex

↓ Run in 1X, elute in 10X Standard Buffer, pool activity, concentrate by Amicon Filtration G-100 Sephadex ↓ Run in 1X Standard Buffer, pool activity, concentrate by Amicon filtration Benzoic Acid Sepharose 1

↓ Elute with 0.1M Sodium Benzoate in 10X Standard Buffer, dialyze against 1X Standard Buffer Benzoic Acid Sepharose 2

↓ Elute with 0 to 0.5M Sodium Benzoate gradient in 10X Standard Buffer, dialyze against 1X Standard Buffer Amicon Filtration Pure Recombinant Luciferase

FIGURE 8

CLONING AND EXPRESSIONS OF *RENILLA* LUCIFERASE

This is a continuation of application Ser. No. 07/933,017, filed Aug. 20, 1992, which is a continuation of U.S. patent application Ser. No. 07/458,952, filed Dec. 29, 1989, both now abandoned.

BACKGROUND OF THE INVENTION

1. Field of the Invention

This invention relates to the field of genetic engineering and is particularly related to the expression of proteins by techniques involving genetic engineering.

2. Description of the Background

The Renilla, also known as sea pansies, belong to a class of coelenterates known as the anthozoans. In addition to Renilla, other representative bioluminescent genera of the class Anthozoa include Cavarnularia, Ptilosarcus, Stylatula, Acanthoptilum, and Parazoanthus. All of these organisms are bioluminescent and emit light as a result of the action of an enzyme (luciferase) on a substrate (luciferin) under appropriate biological conditions. Prior studies have demonstrated that all of the above-mentioned anthozoans contain similar luciferases and luciferins. See, for example, Cormier et al., *J. Cell. Physiol.* (1973) 81: 291–298. The luciferases and luciferins from each of these anthozoans will crossreact with one another to produce the characteristic blue luminescence observed in Renilla extracts. Each of these luciferases has similar biochemical properties, and the biochemical requirements for bioluminescence are identical regardless of the anthozoan from which the luciferase was derived.

There has been considerable interest of late in replacing radioactive labels used in analytical assays with other types, such as luminescent labels. Firefly luciferase, which is a molecule of significantly different structure that does not react with Renilla-like luciferins, is one molecule that has been proposed for use as such labels. However, firefly luciferase suffers from a number of deficiencies that make this molecule less than optimal in biological assays. For example, ATP acts as a trigger of the firefly luciferase system, and the ubiquitous nature of ATP makes control of this variable difficult.

A prior patent application by one of the present inventors, U.S. patent application Ser. No. 059,137, filed Jun. 5, 1987, describes use of coelenterate-derived luciferases and photoproteins as bioluminescent labels. Other applications by the same inventor, for example, U.S. application Ser. Nos. 173,045, filed Mar. 17, 1988, and 165,422, filed Feb. 29, 1988, describe recombinant DNA capable of expressing the photoprotein apoaequorin.

The photoprotein aequorin (which consists of apoaequorin bound to a coelenterate luciferin molecule) and Renilla luciferase both utilize the same coelenterate luciferin, and the chemistry of light emission in both cases has been shown to be the same. However, aequorin luminescence is triggered by calcium, does not require dissolved oxygen, and represents a single turnover event. In contrast, Renilla luciferase is not triggered by calcium and requires dissolved oxygen in order to produce light in the presence of coelenterate luciferin. Renilla luciferase also acts as a true enzyme, catalyzing a long-lasting luminescence in the presence of saturating levels of luciferin.

Sub-attomole levels of aequorin can be detected with photometers even though its luminescence represents a single turnover event. Renilla luciferase, because of its enzymatic ability, should be detectable at levels 1 to 2 orders of magnitude lower than aequorin. Furthermore, Renilla luciferase is known to be relatively stable to heat, an important consideration for assays that often involve incubation at physiological temperatures. Accordingly, Renilla luciferase is a potentially useful label for biological and other assays.

On the other hand, Renilla live on the ocean bottom, about 30 to 100 feet deep, and must be collected by dregging. From 1 kg of Renilla (about 1000 animals), approximately 1 mg of pure Renilla luciferase can be obtained following a tedious procedure which requires purifying the protein about 12,000 fold. The purification procedure is described in Matthews et al., Biochemistry (1977) 16: 85–91. As a result, there has been no development of Renilla luciferase as a detectable label.

Accordingly, improved techniques for the production of pure Renilla luciferase are necessary before this molecule can be used commercially in bioluminescence assays.

BRIEF DESCRIPTION OF THE DRAWINGS

The invention will be better understood by reference to the following detailed description and examples and the attached Figures that form part of the present specification, wherein:

FIG. 1 is the nucleotide sequence of a clone that contains a *Renilla reniformis* luciferase cDNA sequence.

FIG. 2 is the amino acid sequence derived from the open reading frame of the Renilla luciferase cDNA shown in FIG. 1.

FIG. 3 is the recombinant luciferase amino acid sequence with different types of underlining to show the location of peptides obtained by digestion of native luciferase with V-8 protease.

FIG. 4 is a table showing the amino acid sequence of *Renilla reniformis* peptides obtained by V-8 protease digestion. Regions of low degeneracy that were selected for preparation of oligonucleotide probes are shown by boxes. The probes are shown at the bottom part of the Figure.

FIG. 5 is a schematic representation of a restriction enzyme map for Renilla luciferase cDNA. The lower portion of FIG. 5 is a schematic representation of sequencing strategy for Renilla luciferase cDNA.

FIG. 8 is a schematic diagram of the purification scheme used to purify recombinant luciferase.

SUMMARY OF THE INVENTION

Figure 6:
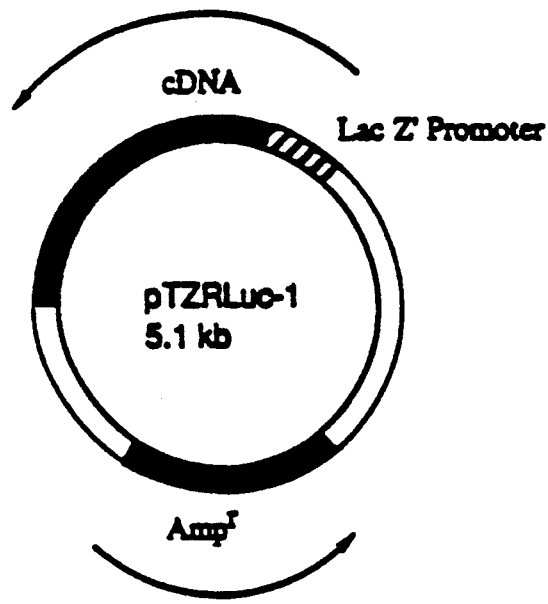
FIG. 6 is a map of a Renilla luciferase expression plasmid.

The present invention provides genetic material encoding Renilla luciferase. The genetic material can be used to produce the enzyme for use as luminescent tags in bioluminescence assays and for other purposes for which such labels are desirable. Additionally, the genetic material can be used as a source of probes that can be used in nucleic acid hybridization assays for the identification of other luciferase genes from related organisms. Fragments of the enzyme can be used to prepare antibodies for the purpose of identifying luciferase genes from related organisms. Specific genetic materials and luciferase proteins are disclosed in the following detailed description and examples.

DESCRIPTION OF SPECIFIC EMBODIMENTS

The present inventors have identified and obtained for the first time genetic material encoding luciferase from the coelenterate genus Renilla which previously has been available only in limited quantities. Since luciferases have a number of uses as a bioluminescent label and since Renilla luciferase has a number of properties that make it particularly useful as a label, availability of the enzyme in significant quantities in pure form provides a significant commercial advantage over prior sources. The Renilla genetic material also provides a source of nucleic acid probes for use in hybridization techniques that allow location of luciferase genes in related organisms. The cDNA sequence for a clone that contains a *Renilla reniformis* luciferase gene is set forth in FIG. 1, with the translated cDNA amino acid sequence being set forth in FIG. 2. The coding sequence of the clone in FIG. 1 begins at nucleotide 10 and continues to a stop codon at nucleotide 944. FIG. 3 shows a complete recombinant Renilla luciferase amino acid sequence as produced by an expression system.

The present invention has specifically contemplated each and every possible variation of polynucleotide that could be made by selecting combinations based on the possible codon choices listed in FIG. 1 (with the reading frame beginning at position 1 of FIG. 1) and in Table 1 (below), and all such variations are to be considered as being specifically disclosed and equivalent to the sequence of FIG. 1. Codons are preferably selected to fit the host cell in which the enzyme is being produced. Selection of codons to maximize expression of proteins in a heterologous host is a known technique.

Other DNA molecules that code for such peptides can readily be determined from the list of codons in Table 1 and are likewise contemplated as being equivalent to the DNA sequence of FIG. 1. In fact, since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

TABLE 1

| GENETIC CODE | |
|---|---|
| Alanine (Ala, A) | GCA, GCC, GCG, GCT |
| Arginine (Arg, R) | AGA, AGG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamine (Gln, Q) | CAA, CAG |
| Glutamic acid (Glu, E) | GAA, GAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal | TAA, TAG, TGA |

Key:
Each 3-letter triplet represents a trinucleotide of DNA having a 5' end on the left and a 3' end on the right. The letters stand for the purine or pyrimidine bases forming the nucleotide sequence: A = adenine, G = guanine, C = cytosine, and T = thymine. The RNA code is the same except that U (uracil) replaces T.

In addition to the specific nucleotides listed in FIG. 1, DNA (or corresponding RNA) molecules of the invention can have additional nucleotides preceding or following those that are specifically listed. For example, poly A can be added to the 3'-terminal; a short (e.g., fewer than 20 nucleotides) sequence can be added to either terminal to provide a terminal sequence corresponding to a restriction endonuclease site, stop codons can follow the peptide sequence to terminate translation, and the like. Additionally, DNA molecules containing a promoter region or other control region upstream from the gene can be produced. All DNA molecules containing the sequences of the invention will be useful for at least one purpose since all can minimally be fragmented to produce oligonucleotide probes and be used in the isolation or detection of DNA from biological sources.

A number of words used in this specification have specific meanings in addition to their more common meanings. "Renilla luciferase" means the luciferase enzyme isolated from a member of the genus Renilla or an equivalent molecule obtained from any other source or synthetically. By "equivalent" is meant, when referring to two nucleotide sequences, that the two nucleotide sequences in question encode the same sequence of amino acids. When "equivalent" is used in referring to two peptides, it means that the two peptides will have substantially the same amino acid sequence. When "equivalent" refers to a property, the property does not need to be present to the same extent (e.g., two peptides can exhibit different rates of the same type of enzymatic activity), but the properties are preferably substantially the same. "Complementary," when referring to two nucleotide sequences, means that the two sequences are capable of hybridizing, preferably with less than 25%, more preferably with less than 15%, even more preferably with less than 5%, most preferably with no mismatches between opposed nucleotides. Preferred hybridizing conditions (which are not limited to specific numbers of mismatches) are set forth in the Examples. The term "substantially" varies with the context as understood by those skilled in the relevant art and generally means at least 70%, preferably means at least 80%, more preferably at least 90%, and most preferably at least 95%. The phrase "substantially identical" includes complete identity as well as less than complete identity (e.g., of amino acid sequences or enzymatic activity) as established by the prior definition of "substantially." The term "isolated" as used herein refers to, e.g., a peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acrylamide gel) but not obtained either as pure substances or as solutions. The phrase "replaced by" or "replacement" as used herein does not necessarily refer to any action that must take place but to the peptide that exists when an indicated "replacement" amino acid is present in the same position as the amino acid indicated to be present in a different formula (e.g., when leucine instead of valine is present at amino acid 11).

Since the DNA sequence of the Renilla luciferase gene has been identified, it is possible to produce a DNA gene entirely by synthetic chemistry, after which the gene can be inserted into any of the many available DNA vectors using known techniques of recombinant DNA technology. Thus, the present invention can be carried out using reagents, plasmids, and microorganisms which are freely available and in the public domain at the time of filing of this patent application without requiring a deposit of genetic material.

For example, nucleotide sequences greater than 100 bases long can be readily synthesized on an Applied Biosystems Model 380A DNA Synthesizer as evidenced by commercial advertising of the same (e.g., Genetic Engineering News, November/December 1984, p. 3). Such oligonucleotides can readily be spliced using, among others, the technique of preparing overlapping complementary sequences (e.g, 1–100 of coding strand, 0–50 and 51–150 of complementary strand, 101–200 of coding strand, etc.), followed by hybridizing and ligating the strands. Such techniques are well known and are described in detail in, for example, Davis et al., *Basic Methods in Molecular Biology*, Elsevier Science Publ. Co., Inc., New York (1986). The peptides can then be expressed in a host organism as described herein.

Furthermore, automated equipment is also available that makes direct synthesis of many of the peptides disclosed herein readily available, especially peptide fragments of less than the entire Renilla luciferase enzyme. In the same issue of Genetic Engineering News mentioned above, a commercially available automated peptide synthesizer having a coupling efficiency exceeding 99% is advertised (page 34). Such equipment provides ready access to the peptides of the invention, either by direct synthesis or by synthesis of a series of fragments that can be coupled using other known techniques.

In addition to the specific polypeptide sequence shown in FIGS. 2 and 3, peptide fragments based on these sequences and fragments and full length sequences representing minor variations thereof will have at least some of the biological activities of luciferase and will therefore be useful in appropriate circumstances. For example, fragments of the luciferase enzyme sequence can readily be prepared and can be screened for use as luciferin binding site models. Peptide synthesizers can be used to prepare small polypeptide fragments (e.g., less than 100 amino acids) or techniques of genetic engineering can be used to prepare larger fragments. A simple screening procedure that will identify suitable polypeptide fragments consists of attaching a suitable substrate, e.g., a coelenterate luciferin molecule, to an affinity column and capturing peptide fragments that are retained by the bound substrate. Such peptides can also be used (and are indeed more likely to be used) as immunogens for the preparation of antibodies that can be used to screen for the expression of a luciferase by a genetically engineered organism, in which case the bound substrate will be an antibody or similar molecule that binds specifically to Renilla luciferase.

The ability to prepare and select peptide fragments having appropriate binding affinity from a larger protein is well known in the art and is described in a number of publications, including patents. See, for example, U.S. Pat. No. 4,629,783, which describes the preparation of immunologically active fragments of viral proteins that bind with the same antibodies as the entire viral protein.

In addition, minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e., a conservative replacement) will not have a major effect on the biological activity of the resulting molecule, especially if the replacement does not involve an amino acid at a binding site or other site of biologic activity. Furthermore, additional amino acids can be present at either of the two termini, or amino acids can be absent from one or both of the termini, as is known in the art.

Whether a change results in a functioning peptide can readily be determined by direct analysis for function in a assay that relies on ability of the modified enzyme (or fragment) to carry out the normal function of the natural luciferase enzyme (or fragment). For example, modified peptides can be tested for ability to catalyze the emission of light from coelenterate luciferin by the same techniques described below for the recombinant Renilla luciferase molecule. Peptides in which more than one replacement has taken place can readily be tested in the same manner. Preferred peptides differ at no more than 12, more preferably no more than 5, amino acids in any contiguous group of 20 amino acids. Substitutions of amino acids, when they occur, are preferably from within standard conservative groups. Standard conservative groups of amino acids are shown in parenthesis using the one-letter amino acid code: nonpolar (A,V,-L,I,P,M); aromatic (F,T,W); uncharged polar (G,S,T,C,N,Q); acidic (D,E); basic (K,R,H). The aromatic amino acids are sometimes considered to belong to the broader-defined nonpolar (F,W) or uncharged polar (T) groups.

Salts of any of the peptides described herein will naturally occur when such peptides are present in (or isolated from) aqueous solutions of various pHs. All salts of peptides having the indicated biological activity are considered to be within the scope of the present invention. Examples include alkali, alkaline earth, and other metal salts of carboxylic acid residues, acid addition salts (e.g., HCl) of amino residues, and zwitterions formed by reactions between carboxylic acid and amino residues within the same molecule.

Although genes and corresponding proteins can be prepared by the totally synthetic techniques discussed above, in preferred embodiments of the invention genetic information is obtained from natural sources and identified as described herein. The genetic material is first obtained in the form of a gene library, using any of numerous existing techniques. The first of these is to randomly shear genomic DNA and insert this sheared material into expression vectors. If enough recombinants are generated, there is a good probability of having at least one recombinant in the population which is expressing a fusion protein corresponding to the enzyme of interest.

Another strategy for preparing gene libraries is to make complementary DNA (cDNA) copies of the total mRNA population of the organism and to clone these as recombinant molecules in expression vectors. The expected nature of the organism (i.e., it was expected to have the characteristics of a eucaryote) indicated that introns might be present within the coding region of the desired gene. Although introns do not preclude use of sheared genomic DNA, they increase the number of recombinants which must be screened and make further analyses substantially complicated. Based on this result, use of a cDNA library to obtain Renilla genes is preferred.

Such a library was generated in the laboratory of the inventors and screened for expression of a gene product having luciferase activity. Details of this example are set forth below, including details of the experiments that lead to obtaining the complete sequence of the gene. However, there is no reason to believe that the sequence and specific engineered organism prepared by the inventors is any better than other clones that can be prepared using the guidance set forth in this specification. In fact, it is likely that expression of Renilla luciferase can be enhanced over that described herein by selection of other expression systems, as discussed in the examples below Now that the sequence of Renilla luciferase has been determined, it is no longer necessary to go through these steps to obtain the genetic material of the present invention. The polymerase chain reaction (PCR) technique can now be used to isolate genes from natural sources in a simpler and more direct manner. The PCR technique, including use in diagnosis, is disclosed in U.S. Pat. No. 4,683,202, which is herein incorporated by reference. Since Renilla specimens are readily available from the oceans of the world, and since PCR probes can be prepared using the sequences set forth in this specification, it is possible to obtain any desired segment of the sequences set forth herein using the PCR technique and naturally available sources of Renilla genomic material. A specific example of such a technique for isolating the Renilla luciferase chromosomal gene is described in the examples that follow. The cloned gene can then be inserted into commercial vectors and expressed.

Although the techniques set forth above, when used in combination with the knowledge of those skilled in the art of genetic engineering and the previously stated guidelines, will readily enable isolation of the desired gene and its use in recombinant DNA vectors now that sufficient information is provided to locate the gene, other methods which lead to the same result are also known and may be used in the preparation of recombinant DNA vectors of this invention.

Expression of Renilla protein can be enhanced by including multiple copies of the gene in a transformed host; by selecting a vector known to reproduce in the host, thereby producing large quantities of protein from exogeneous inserted DNA (such as pUC8; ptac12; pIN-III-ompA1, 2, or 3; pOTS; pAS1; or pKK2233); or by any other known means of enhancing peptide expression.

One common variation is the preparation of a polypeptide of the invention in the form of a fused polypeptide. Such peptides are typically prepared by using the promoter region of a gene known to be expressed in a host and inserting nucleotides that encode all or a major portion of the amino acid sequence of the invention into the genetic sequence for the host protein. Examples of such fused proteins include β-galactosidase fused proteins. If desired, the fused peptide can be designed so that a site recognized by a proteolytic enzyme is present at the junction between the two fused proteins. The proteolytic enzyme can then be used to cleave the expressed protein so that the desired luciferase enzyme is available in pure form.

In all cases, a Renilla luciferase will be expressed when the DNA sequence is functionally inserted into the vector. By "functionally inserted" is meant in proper reading frame and orientation, as is well understood by those skilled in the art. Typically, a gene will be inserted downstream from a promoter and will be followed by a stop codon, although production as a hybrid protein (possibly followed by cleavage) may be used, if desired.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. Pat. Nos. disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

The implications of the present invention are significant in that useful amounts of Renilla luciferase and genetic material of the invention will become available for use in the development of hybridization assays or in any other type of assay utilizing these materials. Transferring the Renilla luciferase cDNA which has been isolated to other expression vectors will produce constructs which improve the expression of luciferase in *E. coli* or express the polypeptide in other hosts.

Particularly contemplated is the isolation of genes from related organisms using oligonucleotide probes based on the principal and variant nucleotide sequences disclosed herein. Such probes can be considerably shorter than the entire sequence but should be at least 10, preferably at least 14, nucleotides in length. Intermediate oligonucleotides from 20 to 500, especially 30 to 200, nucleotides in length provide particularly specific and rapid-acting probes. Longer oligonucleotides are also useful, up to the full length of the gene. Both RNA and DNA probes can be used.

In use, the probes are typically labelled in a detectable manner (e.g., with $^{32}$P, $^3$H, biotin, or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known.

Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

In summary, the inventors have reduced the present invention to practice by isolating and sequencing a cDNA clone for *Renilla reniformis* luciferase. The deduced amino acid sequence from this cDNA, beginning at the first methionine residue, predicts a protein of $M_r$ equal to 36 kd, which is the approximate size of native Renilla luciferase. The deduced amino acid sequence also contains within it all six peptide sequences from V-8 protease-digested native Renilla luciferase. Only one mis-match was found between these two sets of amino acid data, a substitution of a tryptophan for a leucine present in the peptide sequence. Comparisons of the native amino acid composition and the predicted recombinant luciferase composition reveal a very high degree of similarity with many identities between specific amino acid residues.

Additionally, expression of luciferase in a genetically engineered organism has been demonstrated. Luciferase activity was found in crude extracts of the original luciferase clone λRLuc-6. Subcloning the cDNA into the vector pTZ18R increased this activity enough to allow the purification of recombinant luciferase from the pTZRLuc-1 cells. Recombinant luciferase can be purified by a much simplified method from that previously used in the purification of native luciferase. The recombinant luciferase functions identically to native luciferase in all aspects analysed thus far. Like native, recombinant luciferase has an emission spectrum with a λmax at 480 nm and a shoulder at 400 nm. The absorption spectrum of recombinant luciferase is also identical to that of native. Additionally, both native and recombinant luciferase are very stable at 37° C. for several hours as well as having significant stability at 45° C. Using the specific activity determined for native luciferase, protein determinations made based on light emission correlate very well with $A_{280}$ and Lowry protein determinations, suggesting that the specific activity of recombinant luciferase is similar to, if not the same as, that of native luciferase. Finally, amino-terminus amino acid sequence analysis of recombinant luciferase shows an identical sequence to that of the cDNA-predicted amino acid sequence from residues 2 through 18. A significant amount of the recombinant protein is blocked at the amino terminus, probably by N-formyl methionine, which accounts for the inability to determine the amino acid at residue 1.

The invention now being generally described, the same will be better understood by reference to the following examples which are provided for purposes of illustration only and are not to be considered limiting of the invention unless so specified.

EXAMPLES

Assay for Luciferase Activity

Crude supernatants or pure recombinant luciferase samples {10 to 100 µl} were added to 1 ml of luciferase assay buffer {0.5M NaCl, 0.1 M KPO$_4$ pH 7.6, 1 mM EDTA, 0.02% BSA, and 0.004% NaN$_3$} and vortexed in 12×75 mm test tube. Synthetic benzyl luciferin {10 µl of a 2.5 nmol/µl stock} was added to the reaction to give a final concentration of $2.5 \times 10^{-8}$ M, and the mixture was vortexed rigorously for 4–5 sec. The tube was placed immediately in a Turner Model TD-20e luminometer and peak light emission was determined and converted to photons using a $^{63}$Ni radioactive light emission calibration standard.

RNA Isolation and cDNA Synthesis

Live *Renilla reniformis* were collected by bottom trawling in shallow waters off Sapelo Island in the state of Georgia at the University of Georgia Marine Institute. The animals were washed thoroughly in fresh seawater, quick frozen in liquid nitrogen, and stored at −80° C. Frozen Renilla were crushed to a fine powder under liquid nitrogen with a morter and pestle. The powdered tissue was then homogenized with a Waring blender in 4 M guanidine thiocyanate, and total RNA was isolated as described in Chirgwin et al., *Biochemistry* (1970) 18:5294–5299. Total RNA was then passed over an oligo-dT cellulose column to obtain polyadenylated RNA which was stored as an ethanol precipitate at −20° C. Single and double stranded cDNA were synthesized from poly A+ RNA by modification of the Gubler and Hoffman method, Gubler et al., *Gene* (1983) 25:263–269, as described below. Following T-4 polymerase blunting and methylation of the cDNAs, synthetic EcoRI linkers were blunt-end ligated. After digestion with EcoRI, the excess linkers were separated from the cDNAs by low-melt agarose gel electrophoresis. Only cDNA's greater than about 650 bp in length were isolated from the low melt gel.

Construction and Screening of the λgt11 Library

Purified cDNA's were ligated into EcoRI-digested λgt11. The DNA was then packaged using λ phage extracts (Gigapack Plus Kit, Strategene). Several fractions of the packaged library were titered in *E. coli* Y1088 cells; these fractions ranged from 71% to 81% recombinant phage as determined by the lack of IPTG-inducible β-galactosidase activity. The total number of recombinant phage was equal to $2.1 \times 10^6$ pfu (plaque forming units). The primary library was then amplified in *E. coli* Y1088 cells and stored in 7% DMSO at −80° C. The titer of the amplified library was $2.5 \times 10^7$ pfu/ml and was approximately 65% recombinant.

Two 17-base oligonucleotide probes were synthesized based on amino acid sequence data from isolated peptides derived from V-8 protease digested, native

*Renilla luciferase.* Shown in FIG. 4 are the amino acid sequences of the seven V-8 luciferase peptides. The amino acid sequences with the lowest codon redundancy were selected for synthesis of luciferase oligonucleotide Probe #1 and Probe #2, which are shown highlighted with their derived nucleotide sequences (lower portion of FIG. 4). Probe #1 was derived from peptide 7 and contained 32 redundancies, while Probe #2, derived from peptide 1, contained 64 redundancies. The probes were end-labeled with T-4 polynucleotide kinase to high specific activity {$4-9\times10^8$ cpm/$\mu$g}. *E. coli* Y1088 cells were infected with enough phage to give $3\times10^4$ pfu/plate. The infected cells were plated in 6 ml of top agarose onto 150 mm diameter Luria plates containing 50 $\mu$g/ml ampicillin. After overnight incubation at 37° C., the plates were chilled at 4° C. before performing plaque lifts. To eliminate false positive signals, duplicate nitrocellulose filter plaque replicas were prepared from each master plate. Filters were processed by base treatment followed by neutralization in Tris buffer.

The filters were air dried and baked at 80° C. in vacuo. Prehybridization was for at least 6 hours 37° C. in 6X SSC, 50 mM Sodium Phosphate (pH 6.8), 5X Denhardt's, and 100 ug/ml denatured Herring sperm prehybridization solution with the addition of dextran sulfate to a final concentration of 10%. The labeled probes were added to the hybridization solution at 1-2 $\times10^6$ cpm/ml.

Filter washes were done in the presence of tetramethylammonium choride under the conditions described for a 17-base oligonucleotide in Wood et al., *Proc. Nat Acad. Sci. USA* (1985) 82:1585-1588. Each duplicate filter was hybridized to both probes in the first round of screening; in subsequent rounds, the duplicate filters were hybridized to either Probe #1 or Probe #2. All cDNA clones were plaque purified after three or four rounds of screening; phage DNA was isolated from each clone on glycerol step gradients as described in Grossberger, D., *Nuc. Acid, Res.* (1987) 15(16):6737.

DNA Sequence Analysis

All DNA sequence analysis was done in the M13 vectors mp18 and mp19. Single stranded templates were prepared and dideoxynucleotide sequencing was preformed using a Sequenase DNA Sequencing Kit obtained from United States Biochemical Corporation. Sequencing reactions were primed using either the M13 universal primer, a primer which hybridized to extraneous λgtll DNA present in some constructs, or the oligonucleotide probes. Sequence data obtained from both ends of the cDNA was analyzed for six base restriction enzyme sites which were used to generate sequencing subclones (FIG. 5). In this way, the entire 1.2 kb cDNA was sequenced on both strands (lower portion of FIG. 5). All DNA sequences and translated protein sequences were assembled and analyzed using MicroGenie Sequence Software purchased from Beckman.

Expression in *E. coli*

The initial luciferase cDNA clone, λRLuc-6, was in the expression vector λgtll. The clone was amplified in *E. coli* Y1088 cells and the high titer stock was used to make lysogens in *E. coli* Y1089. The λRLuc-6 lysogen was then grown in Luria broth plus ampicillin (50 $\mu$g/ml) at 37° C. The cells were pelleted, resuspended in TE buffer, and lysed with lysozyme (2 mg/ml). The cell debris was then pelleted and the supernatant was assayed for luciferase activity. The 2.2kbp λRLuc-6 insert which included 1 kb of λgtll lacZ DNA attached to the 3' end was isolated on a low-melt gel and subcloned into the EcoRI/SstI sites of pTZ18R (Pharmacia). This construct, pTZRLuc-1, was used in the expression and purification of recombinant Renilla luciferase.

Electrophoretic and Western Analysis

Recombinant luciferase samples were characterized on Commassie-stained SDS-PAGE gels. For Western analysis, the gels were run and transferred to nitrocellulose filters at 30 mA in transfer buffer as described in Burnett, N.W., *Analytical Biochemistry* (1981) 112:195-203. The filters were blocked with 3% BSA and incubated with a 1/1000 dilution of polyclonal rabbit-anti-luciferase antibodies. Next, the filter was washed in TBS and incubated with al/2500 dilution of the secondary antibody, goat-anti-rabbit IgG conjugated to horseradish peroxidase (Bio-Rad). Finally, the filter was washed in TBS and developed with HRP-Color Developing reagent (Bio-Rad).

Emission Spectra

Crude samples of pTZLuc-1 cells were prepared as described previously in this text. The sample was added to 1 ml of luciferase assay buffer; 1 $\mu$l luciferin (917 nmol/$\mu$l) was added at 1-2 minute intervals to maintain the signal. The bioluminescence emission spectra were obtained and corrected using an on-line computerized SPEX fluorimeter. Multiple spectra were scan averaged to give the final spectrum which was measured from 675 nm to 375 nm.

Protein Purification

Purification of recombinant Renilla luciferase from pTZRLuc-1 *E. coli* extracts was accomplished in three chromatographic steps. Recombinant luciferase was purified from pTZRLuc-1 cells as follows: pTZRLuc-1 cells were grown in 20L Luria broth at 37° C. at an OD$_{600}$=0.6 at which time IPTG was added to a final concentration of 0.5 mM; cells continued to grow overnight at 30° C. The cells were harvested by centrifugation, washed in TE, resuspended in 5 ml of 10 mM EDTA (pH 8) per gram of cells, and frozen at −20° C. In a typical purification, 15 to 30 grams of cells were thawed. Lysozyme was added to a final concentration of 4 to 6 mg/ml, and the cells were held on ice for 45 minutes. DNase 1 (10 to 20 mg) was added to the lysate which was sonicated on ice with 1 minute bursts from a Branson Cell Disrupter until 90% of the cells were lysed as evidenced by microscopic examination.

The crude material was clarified by centrifugation at $48\times g$ for 30 minutes and loaded onto the first column. The extract was first run on a DEAE-Cellulose ion-exchange column followed by a G-100 Sephadex gel filtration column and then a Benzoic Acid-Sepharose affinity column. The G-100 column was run in 1X Renilla Standard Buffer (1.5 mM Tris, 1.0 mM EDTA pH 7.8). The other columns were run in 1X buffer and were eluted in 10X buffer (DEAE) or Sodium Benzoate in 10X buffer (Benzoic Acid-Sepharose). The first Benzoic Acid column was eluted with 0.1 M sodium benzoate pulse. The second Benzoic Acid column was eluted with a 0 to 0.5 M sodium benzoate gradient. Protein determinations were made by A$_{280}$ measurements using the extinction coefficient of native luciferase {$\epsilon_{280}$nm0.1% =2.1}, by light emission using the specific activity of naive luciferase {$1.8\times10^{15}$ hv sec$^{-1}$ mg$^{-1}$}, or by Bradford assays as described in Bradford, M., *Analytical Biochemistry* (1976) 72: 248. Absorption spectra were measured and collected on a Varian Model DMS-100 spectrophotometer.

Isolation and Analysis of λRLuc-6

The primary screen of $1 \times 10^6$ recombinant phage resulted in the isolation of nine clones which gave identical autoradiographic signals on both replica filters. Of the nine original positives, only five gave signals on the second screening, and only one of the five hybridized to both probes. The other four hybridized only to Probe #2, which has the greatest sequence redundancy. Restriction enzyme analysis of the five clones revealed that λRLuc-3 and λRLuc-8 were identical and contained a 1.16 kb insert. λRLuc 2, 5, and 6 had insert sizes of 0.8, 2.34 and 1.2 kbp respectively. Only the λRLuc-3 and λRLuc-8 inserts could be exercised from the EcoRI cloning site by EcoRl digestion. The other three inserts had apparently lost one EcoRI linker site; these had to be cut with EcoRI and SstI. Thus, each of these cDNAs contained 1 kb of λgtll DNA attached at one end. Since only λRLuc-6 hybridized to both oligonucleotide probes and contained a cDNA of the size necessary to code for an approximately 36 kd protein, it was chosen for DNA sequence analysis.

The 2.2kb EcoRI/SstI fragment, which contained 1 kb of λgtll lac Z DNA, was subcloned into M13 and mp18 and mp19 and both strands of the 1.2 kb cDNA were completely sequenced. The entire cDNA sequence is 1196 bp, excluding the EcoRI linker (FIG. 1). Structurally, it contains a putative initiation codon beginning at nucleotide 10, a stop codon at nucleotide 944, a polyadenylation consensus sequence at nucleotide 1170, and a short polyadenylated tail of seven nucleotides (FIG. 1). Also shown underlined in FIG. 1 are the two oligonucleotide hybrization sites located at nucleotides 537–554 (Probe #1) and nucleotides 820–836 (Probe #2). The loss of the EcoRI site at the 3' end of the cDNA was confirmed by the sequence analysis.

The cDNA does not contain a stop codon in frame with and upstream from the first initiation codon as an indication that the protein coding region is full length. However, the coding region directs the recombinant systhesis of fully active Renilla luciferase, as discussed below. Translating the cDNA sequence into an amino acid sequence gave conclusive evidence that the λRLuc-6 cDNA was a Renilla luciferase cDNA. The translated cDNA sequence contains an open reading frame of 314 amino acids (FIG. 2). The first methionine is preceded by three amino acids which may or may not be part of the native protein sequence. If the in vivo translation begins at the first methionine, an open reading frame of 311 amino acids results which codes for a protein of molecular weight ($M_r$) ~36 Kd. The $M_r$ of native Renilla luciferase has been measured by various methods with values ranging from 33 Kd to 38 Kd. Comparing the amino acid composition of this translated amino acid sequence with that of the previously published native luciferase composition shows a very close homology with many identities between the two (Table 2).

TABLE 2
Amino Acid Composition of Native and Recombinant *Renilla reniformis* Luciferase

| Amino Acids | Residues (Native) | Residues (Recombinant) |
|---|---|---|
| Lysine | 26 | 27 |
| Histidine | 10 | 10 |
| Arginine | 12 | 13 |
| Aspartate* | 31 | 30 |
| Threonine | 9 | 6 |
| Serine | 20 | 19 |
| Glutamate** | 36 | 37 |
| Proline | 17 | 18 |
| Glycine | 19 | 17 |
| Alanine | 19 | 19 |
| Valine | 23 | 23 |
| Methionine | 7 | 9 |
| Isoleucine | 20 | 21 |
| Leucine | 23 | 22 |
| Tyrosine | 12 | 13 |
| Phenylalanine | 15 | 15 |
| Tryptophan | 7 | 8 |
| Cysteine | 3 | 3 |

*Aspartate + Asparagine
**Glutamate + Glutamine
Native luciferase composition data taken from Matthews et al., Biochemistry (1977) 16: 85–91.

Further evidence that the cDNA does code for luciferase can be seen by comparing the V-8 protease peptide sequences with the translated cDNA sequence (FIG. 3). All V-8 peptides were located on the carboxyl-terminal half of the translated coding region beginning at residue 161; several overlapped with one another. Except at one residue, 219, where the cDNA sequence predicts a tryptophan but peptide 6 sequence indicates a leucine at the same position, all peptides matched exactly to regions of the translated sequence. Bunching of the peptides at one end of the protein sequence may be due to the amino-terminal half of the native protein being folded in such a way as to be inaccessible to V-8 protease.

Expression of Recombinant Luciferase in *E. coli*

The original λRLuc 6 lysogen showed low levels of luciferase activity as determined by light emission IPTG induction of λRLuc-6 lysogens led to an approximate 50% decrease in activity. This result was later explained when DNA sequence data revealed that the 3' end of the cDNA was adjacent to the lac Z sequence in λgtll. Therefore, under conditions of IPTG induction, transcription was being forced in the wrong direction with respect to the luciferase cDNA orientation. Presumably, the non-induced luciferase expression in this construct was due to promoter activity from the left end of λgtll at a site which we have not determined.

The construct pTZRLuc-1 was made to simplify the isolation of DNA fragments for use as probes in Southern and Northen analysis (FIG. 6). *E. coli* cells harboring this plasmid are referred to as pTZRLuc-1 cells. Similar to λgtll, the pTZ series "phagemids" contain a polylinker site adjacent to the lac Z' gene. Expressed genes in this vector could potentially be expressed containing the first 10 to 15 amino acids of β-galactosidase fused to the cDNA translation product. Analysis of pTZRLuc-1 cell supernatants for light emission showed that, relative to λRLuc-6, high levels of luciferase activity were present. Furthermore, induction of pTZRLuc-1 cells with 0.5 mM IPTG led to an increase in luciferase activity of ~5-8 fold in crude extracts.

The bioluminescence emission spectrum from these crude supernatants was identical to the previously published bioluminescence emission spectrum for native Renilla luciferase. The wavelength distribution of light emission is essentially identical to that reported earlier. The spectrum had an emission maximum ($\lambda$max) at 480 nm with a slight shoulder at 400 nm, which presumably corresponded to the luciferase-oxyluciferin complex neutral species excited state.

The pTZRLuc-1 crude supernatants were further characterized by SDS-PAGE. The Coomassie-stained gel contained numerous bands, one of which ran in the vicinity of native luciferase. To confirm that this band was recombinant lucifers, Western analysis was performed using rabbit polyclonal antibodies raised against native Renilla luciferase. The developed Western showed one band that migrated at the same position as native luciferase. No other products indicative of $\beta$-galactosidase-luciferase fusion polypeptide were apparent, suggesting that either any putative fusion protein is in too low a concentration to be detected or, more likely, that no fusion protein is made. Though it has not been confirmed by DNA sequence analysis, any pTZRLuc-1 translation products initiating at the $\beta$-galactosidase ATG start codon within the first three codons immediately adjacent to the first cDNA start codon may explain why we see IPTG induction of luciferase activity without production of a fusion product.

Figure 7:
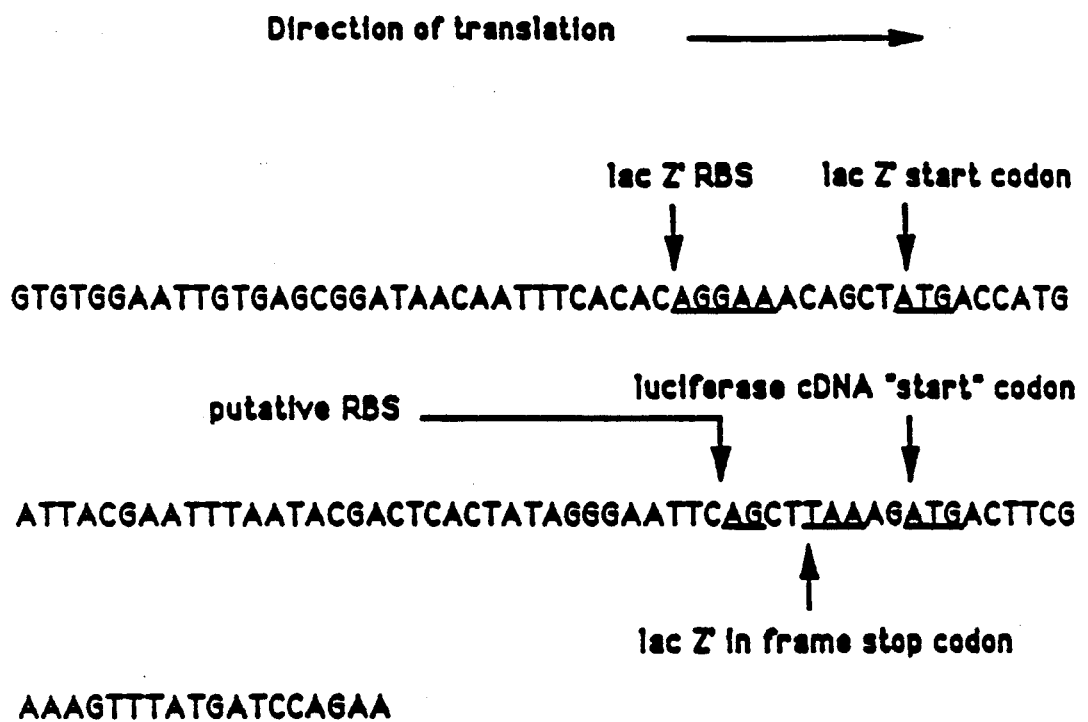
FIG. 7 is a schematic diagram of the control region of the plasmid pTZRLuc-1.

IPTG induction of recombinant luciferase indicates that its transcription is directed by the lac Z promoter. Since the only candidate ribosome binding site (RBS) is probably positioned too far (18 nucleotides) from the luciferase ATG to be functional, we suspect that a $\beta$-galactosidase peptide is being translated to the stop codon immediately adjacent to the luciferase ATG. The translation of a $\beta$-galactosidase peptide may facilitate ribosome reinitiation at the luciferase ATG codon (FIG. 7). This event could occur if the dinucleotide AG was acting as a RBS for the luciferase cDNA. In this way an IPTG inducible, non-fusion luciferase polypeptide could be synthesized. Given the success of recombinant luciferase expression using the pTZ18 vector, which was designed as a multi-purpose in vitro transcription vector rather than an expression vector, it is obvious that other clones can be developed which express luciferase at levels greater than those which we currently obtain.

Purification of Recombinant Renilla Luciferase

Using the specific activity for native luciferase, we made calculations for the amount of luciferase present in IPTG induced, pTZRLuc-1 crude supernatants and determined that the amount of recombinant luciferase being produced was sufficient to attempt initial purification on a small scale.

In IPTG induced pTZRLuc-1 cells, recombinant luciferase represents approximately 12-14% of the total protein in the clarified crude supernatant. Although significant losses of recombinant luciferase were suffered in this initial purification, the amount of starting material and time involved made the loss seem insignificant when compared to the purification of native luciferase. The purification scheme for the recombinant Renilla luciferase is shown in FIG. 8; the purification is summarized in Table 3. SDS-PAGE analysis of the purification steps shows increasing amounts of recombinant luciferase with respect to contaminating protein. The Benzoic Acid-Sepharose luciferase is approximately 99% pure as evidenced by a single band of $M_r$ equal to 34 Kd. Very slight contamination was noticible on the Coomassie stained gel if more than 20 $\mu$g of protein were loaded.

TABLE 3

| Step | Vol (ml) | Protein (mg) | Activity* | Sp. Act.** | Purification | Yield (%) |
|---|---|---|---|---|---|---|
| | | | Recombinant Luciferase Purification | | | |
| CRUDE | 138 | 1120 | $3.2 \times 10^{17}$ | $2.9 \times 10^{14}$ | 0 | 100 |
| DEAE | 48 | 268 | $9.1 \times 10^{16}$ | $3.3 \times 10^{14}$ | 1.1 | 27 |
| G-100 | 675 | 148 | $1.9 \times 10^{16}$ | $1.3 \times 10^{14}$ | .43 | 5.8 |
| B.A.(1) | 55 | 26.4 | $4.5 \times 10^{16}$ | $1.7 \times 10^{15}$ | 5.8 | 13.8 |
| B.A.(2) | 28 | 10.45 | $1.9 \times 10^{16}$ | $\sim 1.8 \times 10^{15}$ | 6.3 | 5.9 |

*Activity in units of hv sec$^{-1}$
**Specific Activity in units of hv sec$^{-1}$ mg$^{-1}$ The absorption spectrum of pure recombinant luciferase is also identical to that of native luciferase. Based on the specific activity of native luciferase, the protein concentration of recombinant luciferase determined by light emission correlated very well with protein concentration based on $A_{280}$ and Lowry measurements. This results suggests that the specific activity of recombinant luciferase is the same as native. Native Renilla luciferase has been shown previously to exhibit temperature stability at 37° C. and 45° C. The recombinant protein has also been analyzed for temperature stability and, like native luciferase, is stable at 37° C. for several hours and 45° C. for shorter periods of time without significant loss of activity. Stability at these temperatures is an important feature for the utility of recombinant luciferase in diagnostic applications, many of which require incubation at physiological temperatures.

Purification of recombinant Renilla luciferase has allowed us to determine its amino-terminal sequence. The amino acid sequence of the first 18 residues was determined by Edman degradation. The amino acid peak heights of the sequence data indicated that far less protein was actually being sequenced than was initially protein synthesis, it may be that a large percentage of recombinant luciferase is N-formylated at the initiating methionine and thus blocked to the Edman reaction. In spite of this apparent amino-terminal block, enough unblocked species were available that we were able to obtain sequence for the first 18 residues of recombinant luciferase. The amino acid sequence is identical to the translated cDNA sequence from residues 2 through 18 (FIG. 7). On cycle 1 of the amino acid sequencing run, we were not able to confirm the presence of a methionine at the first residue as predicted by the cDNA sequence. However, the fact that the two sets of amino acid data are identical from amino acid residue 2 (Threonine) to residue 18 (Proline) strongly supports our assertion that the first predicted methionine in our sequence is acting as the initiation codon in the pTZRLuc-1 construct.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated DNA or RNA molecule consisting essentially of a nucleotide sequence encoding a Renilla luciferase.

2. The molecule of claim 1, wherein said molecule consists essentially of luciferase coding sequence:
AGCTTAAAGATGACTTCGAAAGTTTATGATCCAGAACAAAGGAAACTTAT GATAACTGGTCCGCACTGGTGGGCCAGATGTAAACAAATGAATGTTCTTG ATTCATTTATTAATTATTATGATTCAGAAAAACATGCAGAAAATGCTGTT ATTTTTTTACATGGTAACGCGGCCTCTTCTTATTTATGGCGACATGTTGT GCCACATATTGAGCCAGTAGCGCGGTGTATTATACCAGATCTTATTGGTA TGGCAAATCAGGCAAATCTGGTAATGGTTCTTATAGGTTACTTGATCAT TACAAATATCTTACTGCATGGTTTGAACTTCTTAATTTACCAAAGAAGAT CATTTTTGTCGGCCATGATTGGGGTGCTTGTTTGGCATTTCATTATAGCT ATGAGCATCAAGATAAGATCAAAGCAATAGTTCACGCTGAAAGTGTAGTA GATGTGATTGAATCATGGGATGAATGGCCTGATATTGAAGAAGATATTGC GTTGATCAAATCTGAAGAAGGAGAAAAATGGTTTTGGAGAATAACTTCT TCGTGGAAACCATGTTGCCATCAAAAATCATGAGAAAGTTAGAACCAGAA GAATTTGCAGCATATCTTGAACCATTCAAAGAGAAAGGTGAAGTTCGTCG TCCAACATTATCATGGCCTCGTGAAATCCCGTTAGTAAAAGGTGGTAAAC CTGACGTTGTACAAATTGTTAGGAATTATAATGCTTATCTACGTGCAAGT GATGATTTACCAAAAATGTTTATTGAATCGGATCCAGGATTCTTTTCCAA TGCTATTGTTGAAGGCGCCAAGAAGTTTCCTAATACTGAATTTGTCAAAG TAAAAGGTCTTCATTTTTCGCAAGAAGATGCACCTGATGAAATGGGAAAA TATATCAAATCGTTCGTTGAGCGAGTTCTCAAAAATGAACAA or an essentially equivalent DNA or RNA sequence.

3. The molecule of claim 2, wherein said molecule is DNA.

4. The molecule of claim 3, wherein said molecule contains said luciferase sequence.

5. The molecule of claim 2, wherein said molecule is RNA and contains a sequence equivalent to said luciferase sequence.

6. An expression construct comprising,
a nucleotide sequence encoding a Renilla luciferase; and a promoter sequence 5' to said nucleotide sequence, wherein said promoter sequence functions with said nucleotide sequence to express said nucleotide sequence in a host microorganism.

7. The molecule of claim 6, wherein at least one copy of said sequence is present in a recombinant DNA or RNA vector.

8. A genetically engineered microorganism, wherein said microorganism comprises the vector of claim 7, and is capable of producing biologically active luciferase.

9. The microorganism of claim 8, wherein said microorganism is an *E. coli* strain.

* * * * *